(12) United States Patent
Mohr et al.

(10) Patent No.: US 9,542,529 B2
(45) Date of Patent: Jan. 10, 2017

(54) MEDICAL IMAGE DATA PROCESSING APPARATUS AND METHOD

(71) Applicant: Toshiba Medical Systems Corporation, Otawara-shi (JP)

(72) Inventors: Brian Mohr, Edinburgh (GB); Malcolm Campbell, Edinburgh (GB); Colin Roberts, Edinburgh (GB)

(73) Assignee: Toshiba Medical Systems Corporation, Otawara-shi (JP)

( * ) Notice: Subject to any disclaimer, the term of this patent is extended or adjusted under 35 U.S.C. 154(b) by 37 days.

(21) Appl. No.: 14/068,383

(22) Filed: Oct. 31, 2013

(65) Prior Publication Data

US 2015/0117727 A1    Apr. 30, 2015

(51) Int. Cl.
*G06F 19/00* (2011.01)
*G06T 7/00* (2006.01)

(52) U.S. Cl.
CPC .......... *G06F 19/321* (2013.01); *G06T 7/0024* (2013.01); *G06T 2207/10072* (2013.01)

(58) Field of Classification Search
None
See application file for complete search history.

(56) References Cited

U.S. PATENT DOCUMENTS

| 7,693,349 | B2 * | 4/2010 | Gering | G06K 9/6203 382/282 |
| 8,644,575 | B2 * | 2/2014 | Piper | A61B 6/507 382/131 |
| 8,672,836 | B2 * | 3/2014 | Higgins | A61B 1/00009 345/427 |
| 2003/0013951 | A1 * | 1/2003 | Stefanescu | G06F 17/30256 600/407 |
| 2008/0095465 | A1 * | 4/2008 | Mullick | G06K 9/6206 382/284 |
| 2011/0178394 | A1 * | 7/2011 | Fitzpatrick | G06T 7/0028 600/424 |
| 2013/0182925 | A1 * | 7/2013 | Razeto | A61B 6/03 382/131 |
| 2014/0003690 | A1 * | 1/2014 | Razeto | G06T 7/003 382/131 |

(Continued)

FOREIGN PATENT DOCUMENTS

CN  103202705 A  7/2013
JP  2009-247535  10/2009

(Continued)

OTHER PUBLICATIONS

S Henn and K Witsch, "Multimodal image registration using a variational approach," SIAM J. Sci. Comput. vol. 2, No. 4, pp. 1429-1447, Dec. 19, 2003.*

(Continued)

*Primary Examiner* — Matthew Bella
*Assistant Examiner* — Soo Shin
(74) *Attorney, Agent, or Firm* — Oblon, McClelland, Maier & Neustadt, L.L.P.

(57) ABSTRACT

A medical image data processing apparatus comprises a registration unit configured to perform a non-rigid registration of a first set of medical image data and a second set of medical image data, wherein the registration unit is further configured to determine, for at least one region, a rigid or affine registration that is an approximation of the non-rigid registration.

19 Claims, 9 Drawing Sheets

(56) References Cited

U.S. PATENT DOCUMENTS

| 2014/0073907 A1* | 3/2014 | Kumar | A61B 10/00 |
| | | | 600/414 |
| 2014/0155730 A1* | 6/2014 | Bansal | G01V 3/14 |
| | | | 600/409 |
| 2014/0212014 A1* | 7/2014 | Kim | G06T 3/0068 |
| | | | 382/131 |

FOREIGN PATENT DOCUMENTS

| JP | 4493436 | 4/2010 |
| JP | 4576228 | 8/2010 |
| JP | 2011-41656 | 3/2011 |

OTHER PUBLICATIONS

P Fillard, J-C Souplet, and N Toussaint, "Medical Image Navigation and Research Tool by INRIA (MedINRIA 1.9) Tutorial v2.0," INRIA Sophia Antipolis—Research Project ASCLEPIOS, Oct. 1, 2009.*

A McKenzie, SV Lombeyda, and M Desbrun, "Vector Field Analysis and Visualization through Variational Clustering," Eurographics—IEEE VGTC Symposium on Visualization (2005), pp. 1-7.*

Alexander McKenzie, et al., "Vector Field Analysis and Visualization through Variational Clustering", EUROGRAPHICS—IEEE VGTC Symposium on Visualization, Jun. 1-3, 2005, 7 pages.

J. Kim, et al., "Visual tracking of treatment response in PET-CT image sequences", Int J CARS 6 (Suppl 1), 2011, 2 pages.

William R. Crum, et al., "Information Theoretic Similarity Measures in Non-Rigid Registration", Proceedings of IPMI, 2003, 10 pages.

Office Action issued Aug. 2, 2016, in Chinese Patent Application No. 201410602536.0.

* cited by examiner

MEDICAL IMAGE DATA PROCESSING APPARATUS AND METHOD

FIELD

Embodiments described herein relate generally to a system for, and method of, registration of image data sets. Embodiments may be used, for example, in synchronous navigation of two or more medical images that may be displayed together.

BACKGROUND

It is often desirable when viewing images obtained from volumetric medical image data to view simultaneously images for the same patient or other subject. The anatomy displayed in each image may be largely identical, but the pathology or other properties of the anatomy may differ.

The different images may be obtained from scans or other measurements on the patient or other subject performed at different times, such that there may be differences in a pathology or other condition between the images as the pathology or other condition develops over time. Alternatively, the different images may be obtained from multiple phases of the same set of scans taken during a single measurement procedure, for example images of parts of the respiratory, cardiac or vascular systems at different times during a respiratory or cardiac cycle.

In each case, there may be movement of anatomical structures between the phases or times when the images were obtained. In the case of images obtained at different phases of a respiratory, cardiac or vascular cycle, there may be expansion or contraction of different anatomical structures.

It can be desirable for a radiologist or other operator to be able to navigate synchronously through the different, simultaneously displayed images. For example if two images are displayed, each in a respective display window, and the operator moves one image in its display window they may desire the other simultaneously displayed image to move automatically in the same or similar fashion in its display window. Thus, for example, the same or corresponding anatomical features may be displayed at corresponding positions in both display windows.

In another example if a display indicator, such as a pointer, cross-hairs or cursor is displayed on each of two medical images, it may be desired to synchronise movement of the display indicator on each image, relative to the anatomy displayed in each image. Thus, for example anatomy under MPR (Multi-Planar Reformat) cross-hairs may be aligned, scale and rotation of MPR views may be aligned, or anatomy under cursors may be aligned in different images regardless of movement of the images, cross-hairs or cursors.

When the differences between the sets of image data used to produce the different images are sufficiently large, it can be necessary to register the sets of image data to define a spatial (anatomical) relationship between the simultaneously displayed images, so that substantially the same anatomy can be displayed in substantially the same position in each image. Such registration may be required, for example, if the acquisitions of the images are widely separated in time or if there is significant movement of the anatomy between images.

Registration of image data sets can be performed either manually or automatically using known image analysis techniques.

It is preferred that the radiologist or other operator should not have to manually register the images or manually adjust registration while viewing the images as this can add significant time to the interpretation process.

In the case of automatic registration techniques used in synchronous navigation, it is known to apply a transformation obtained from a rigid or affine registration to display indicators, such as cursors, cross-hairs or pointers, in an attempt to ensure that the position of the display indicator is mapped between different simultaneously displayed images and that the movement of the display indicator is uniform between the different images.

A rigid registration in this context may be considered to be a registration in which the co-ordinates of data points in one data set are subject to rotation, translation and/or scaling in order to register the data set to another data set. An affine registration in this context may be considered to be a registration in which the coordinates of data points in one dataset are subject to rotation, translation, scaling and/or shearing in order to register the dataset to another dataset. Thus, a rigid registration may be considered to be a particular type of affine registration.

It is also known to apply registrations obtained from a rigid registration to the synchronised movement of the simultaneously displayed images themselves, such that the relative appearance of the images is rotated, scaled and/or translated. Generally that does not affect diagnostic quality of image as relative proportion of anatomy is not affected.

Rigid registrations can be performed using an average of data points over the full volume in question, or relative to specific fiduciary points or small anatomical region. However, such registrations may be inaccurate away from fiduciary point(s) or specific anatomical regions. Furthermore, the radiologist or other operator will usually have to make several manual adjustments to registration while viewing the images depending on the anatomical region of interest. Manual adjustments to registration are time consuming and lead to an increase in the time required to view the images. Furthermore, there can be significant issues when analysing small structures across multiple time points (for example, lung nodule tracking).

An example of a problem that can arise from use of rigid registration is illustrated schematically when navigating through images derived from volumetric data sets in FIGS. 1a and 1b.

FIG. 1a shows schematically a series of slices 2a, 2b through a lung volume 4a, 4b obtained from scans at the current time and a prior time. The scans are taken during different breath holds by the patient and, in this case, the lungs are less full at the current time than they were at the prior time. The volumes are registered using a rigid registration. Two of the slices 6a, 6b from the current scan and the prior scan that, according to the rigid registration represent the same region of the lung, are selected for display, as shown in FIG. 1a.

The user then navigates through the volume using known image processing and navigation techniques, and a further two slices 8a, 8b from the current scan and the prior scan that, according to the rigid registration, represent the same region of the lung, are selected for display. In this case it can be seen that the slice 8a selected from the current scan data is at a position outside the lung. Due to the limitations of the rigid registration, navigation has become out of synchronisation with anatomy. In this case it would be necessary for the operator to make a time-consuming manual adjustment of the registration.

In alternative automatic registration techniques, it is also known to apply a transformation obtained from a non-rigid registration to navigation of images or to display indicators, such as cursors, cross-hairs or pointers, again in an attempt to ensure movement of the display indicator or navigation through the images is synchronised. Such non-rigid registrations usually provide a local deformation field, which is not dependent on fiduciary points or anatomical region. However, generally it can be problematic to apply such non-rigid registrations to images if the images are to be used for diagnostic purposes, as the non-linear mapping can cause a distortion of the images that can interfere with diagnosis. Furthermore, the use of non-rigid registrations to display indicators such as cursors, cross-hairs or pointers can lead to non-uniform navigation between studies and can be confusing or misleading.

Non-rigid registrations include free-form registrations, in which the coordinates of data points in one datasets are subject to a flexible, free-form deformation in order to register the dataset to another dataset. Freeform transformations may be defined using dense vector fields, defining an individual displacement for each voxel in a three-dimensional data set. Freeform transformations may also be defined using other fields or functions, for example using B spline functions or thin plate spline functions.

An example of a problem that can arise from use of non-rigid registration is illustrated schematically when navigating through images derived from volumetric data sets in FIGS. 2a and 2b.

FIG. 2a shows schematically a series of slices 12a, 12b through a lung volume 14a, 14b obtained from scans at the current time and a prior time. The scans are taken during different breath holds by the patient and, as with FIG. 1a, the lungs are less full at the current time than they were at the prior time. The volumes are registered using a non-rigid registration in this case. Two of the slices 16a, 16b from the current scan and the prior scan that, according to the non-rigid registration represent the same region of the lung, are selected for display, as shown in FIG. 2a.

The user then navigates gradually, slice-by-slice through the volume using known image processing and navigation techniques, until a further two slices 18a, 18b from the current scan and the prior scan that, according to the non-rigid registration, represent the same region of the lung, are displayed. In this case, the use of the non-rigid registration causes non-linear movement and some of the image slices of the prior image data set are skipped as the user navigates through the images, which can be confusing or misleading for the user.

BRIEF DESCRIPTION OF THE DRAWINGS

Embodiments are now described, by way of non-limiting example only, and are illustrated in the following figures, in which.

DETAILED DESCRIPTION

Certain embodiments provide a medical image data processing apparatus comprising a registration unit configured to perform a non-rigid registration of a first set of medical image data and a second set of medical image data, wherein the registration unit is further configured to determine, for at least one region, a rigid or affine registration that is an approximation of the non-rigid registration.

Certain embodiments provide a method of processing medical image data comprising performing a non-rigid registration of a first set of medical image data and a second set of medical image data and, for at least one region, determining a rigid or affine registration that is an approximation of the non-rigid registration. Certain embodiments also provide a non-transitory computer program product comprising machine-readable instructions that are executable to perform the method.

Figure 1A:
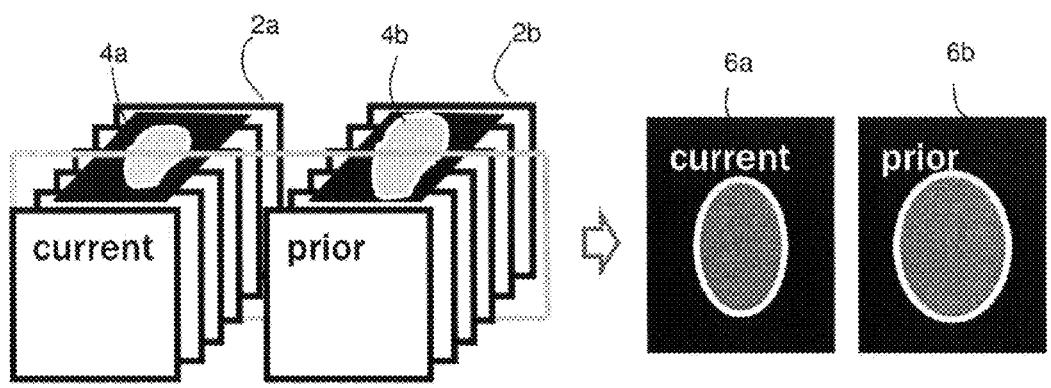
FIGS. 1a and 1b are schematic illustrations showing a series of slices through a lung volume obtained from scans at the current time and a prior time, and each showing two slices selected for display.
Figure 1B:
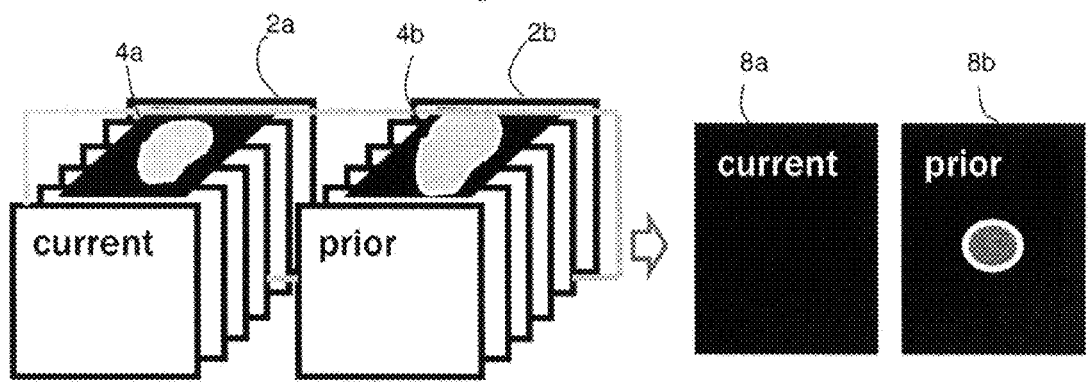
Figure 2A:
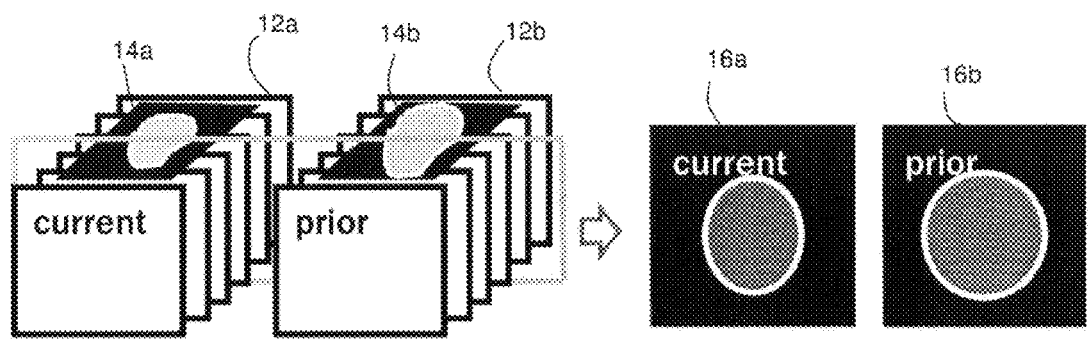
FIGS. 2a and 2b are schematic illustrations showing a series of slices through a lung volume obtained from scans at the current time and a prior time, and each showing a further two slices selected for display.
Figure 2B:
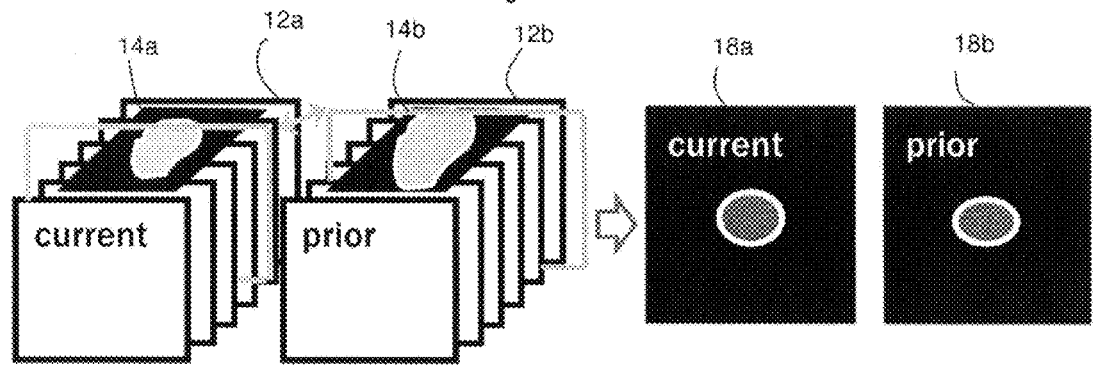
Figure 3:
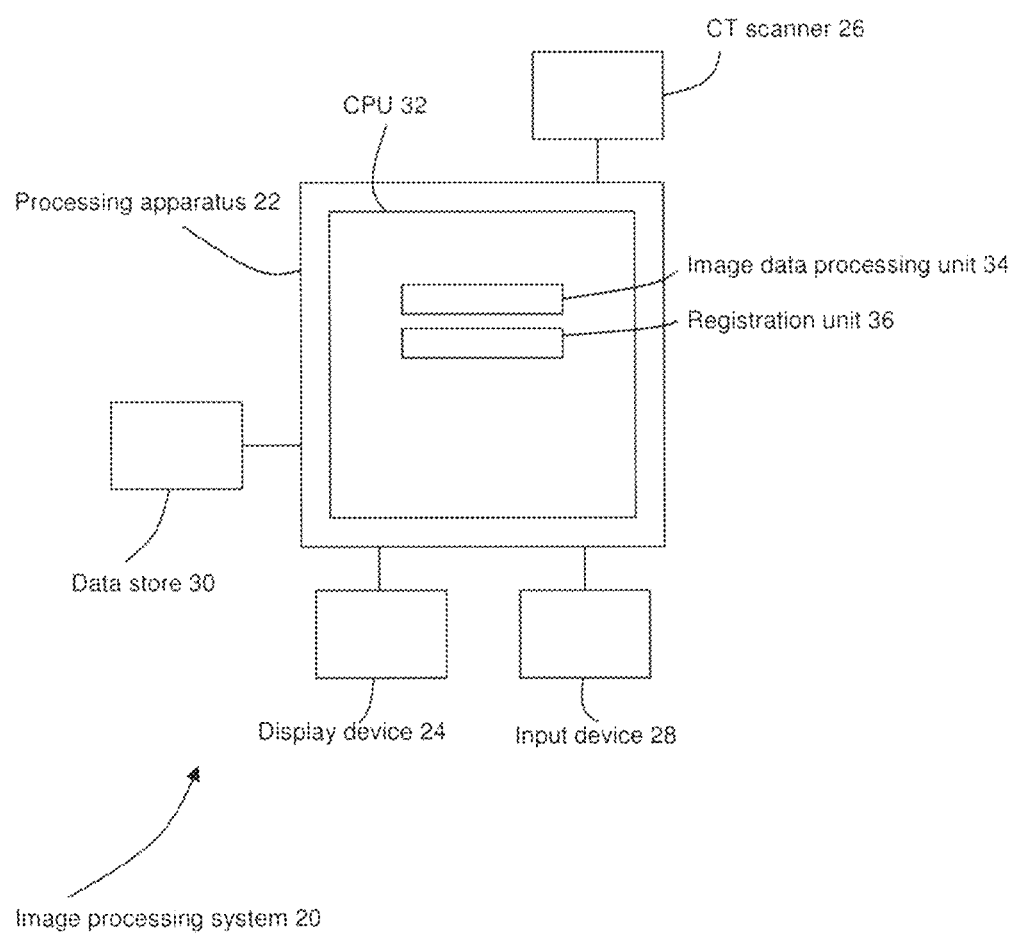
FIG. 3 is a schematic illustration of a medical image processing system according to an embodiment.

A medical image processing system 20 according to an embodiment is illustrated schematically in FIG. 3 and comprises a processing apparatus 22 configured to implement a method as described above. In the embodiment shown in FIG. 3, the processing apparatus 20 may comprise a personal computer (PC) or workstation, or any other suitable type of general purpose or dedicated computing device. The processing system 20 further comprises a display device 24, a CT scanner 26 and a user input device or devices 28, in this case a computer keyboard and mouse. The system 1 also includes a data store 30.

Any suitable type of CT scanner may be used that is able to perform 3D CT measurements on a patient or other subject, for example one of the Aquilion® series of scanners produced by Toshiba Medical Systems Corporation. Although the embodiment of FIG. 3 is described in relation to CT scan data, any other suitable type of scanner producing any suitable type of image data may be used in alternative embodiments, for example MRI or PET data of suitable form.

The processing apparatus 22 provides a processing resource for automatically or semi-automatically processing image data, and comprises a central processing unit (CPU) 32 that is able to load and operate a variety of software units or other software components that are configured to perform a method as described in detail below with reference to FIG. 4. The processing apparatus may be configured to provide a variety of image data processing and visualisation techniques for processing and visualising volumetric medical image data, including for example, segmentation, registration and volume rendering.

The software units include an image data processing unit 34 for receiving image data and performing a variety of processing techniques, including for example segmentation and rendering if desired. The software units also include a registration unit 36.

The processing apparatus 22 includes a hard drive and other components of a PC including RAM, ROM, a data bus, an operating system including various device drivers, and hardware devices including a graphics card. Such components are not shown in FIG. 3 for clarity. Any other suitable processing apparatus may be used in alternative embodiments.

In the embodiment of FIG. 3 volumetric image data sets are received by the processing apparatus 22 from the CT scanner 26 following acquisition of scans by the scanner 26, and are stored in the data store 30 and processed by the processing apparatus 22.

In a variant of the embodiment of FIG. 3, the processing apparatus 22 receives volumetric or other image data sets from a remote data store (not shown). The remote data store may store a large number of different data sets obtained from many different scanners over an extended period of time together with associated patient data, for example a data store forming part of a Picture Archiving and Communication System (PACS).

Figure 4:
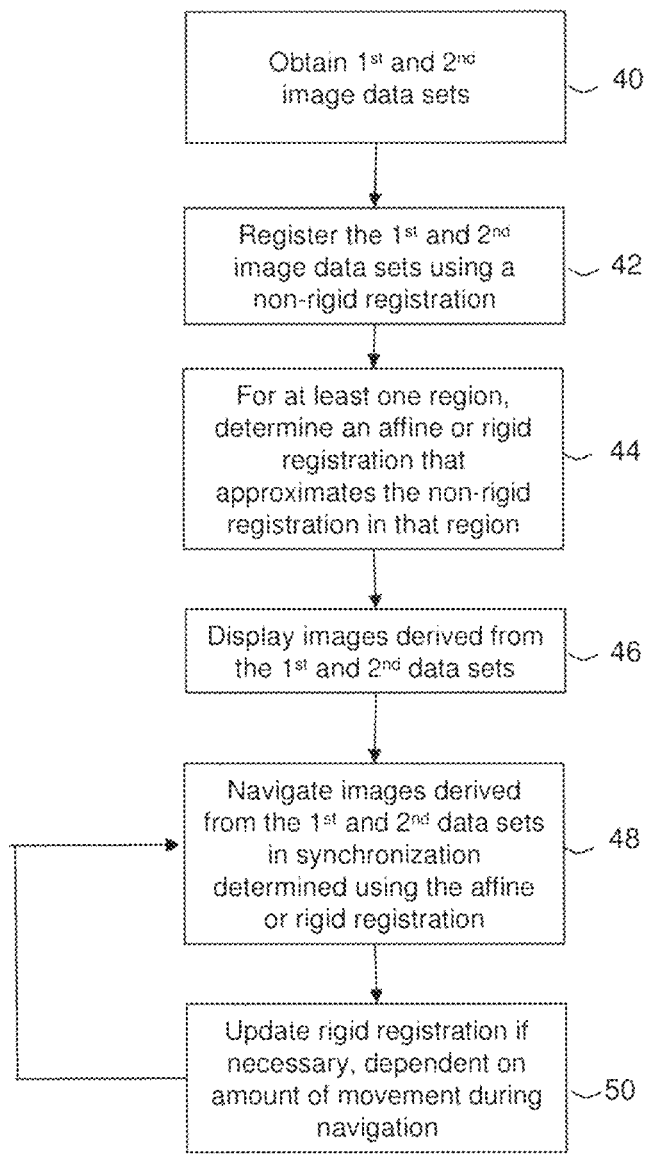
FIG. 4 is a flow chart illustrating in overview a mode of operation of the embodiment of FIG. 3.

The system of FIG. 3 is configured to perform a method of medical image processing having a sequence of stages as illustrated in overview in the flow chart of FIG. 4.

At the first stage 40 of the process, the image data processing unit 34 receives $1^{st}$ and $2^{nd}$ image datasets obtained, in this example, from CT scans performed on the same region of a patients anatomy at different times.

The registration unit 36 then, at stage 42, registers the first and second image datasets using any suitable non-rigid registration procedure. In this case, the global non-rigid registration procedure uses Mutual Information as a similarity measure, and a non-rigid warpfield is computed using the Crum-Hill-Hawkes scheme (William R. Crum, Derek L. G. Hill, David J. Hawkes. Information Theoretic Similarity Measures in Non-rigid Registration, Proceedings of IPMI'2003, pp. 378-387). Any other suitable non-rigid registration procedure may be used in alternative embodiments.

At the next stage 44, the registration unit 36 determines at least one region for which the non-rigid registration determined at stage 42 can be approximated within a predetermined measure of accuracy by an affine or rigid registration. In the present example a rigid registration is used, but in alternative modes of operation an affine registration may be used. The predetermined measure of accuracy may comprise one or more thresholds, and the registration unit 36 may be configured to compare a measure of difference between the non-rigid registration and the rigid or affine registration for data in the region to the one or more thresholds. Any other measure of accuracy may be used, in accordance with any known statistical measures.

In the embodiment of FIG. 3, the process at stage 44 comprises computing approximately homogeneous regions of the non-rigid registration deformation field, using a variational clustering or vector field analysis technique, for example similar to k-means techniques. Examples of techniques that can be used to perform vector field analysis and variational clustering are described, for example, in McKenzie, A., Lombeyda, S., Desbrun, M., "Vector Field Analysis and Visualization through Variational Clustering," IEEE VGTC Symposium of Visualization 2005, 1-3 Jun. 2005, Leeds, UK, Eurographics 2005.

Figure 5:
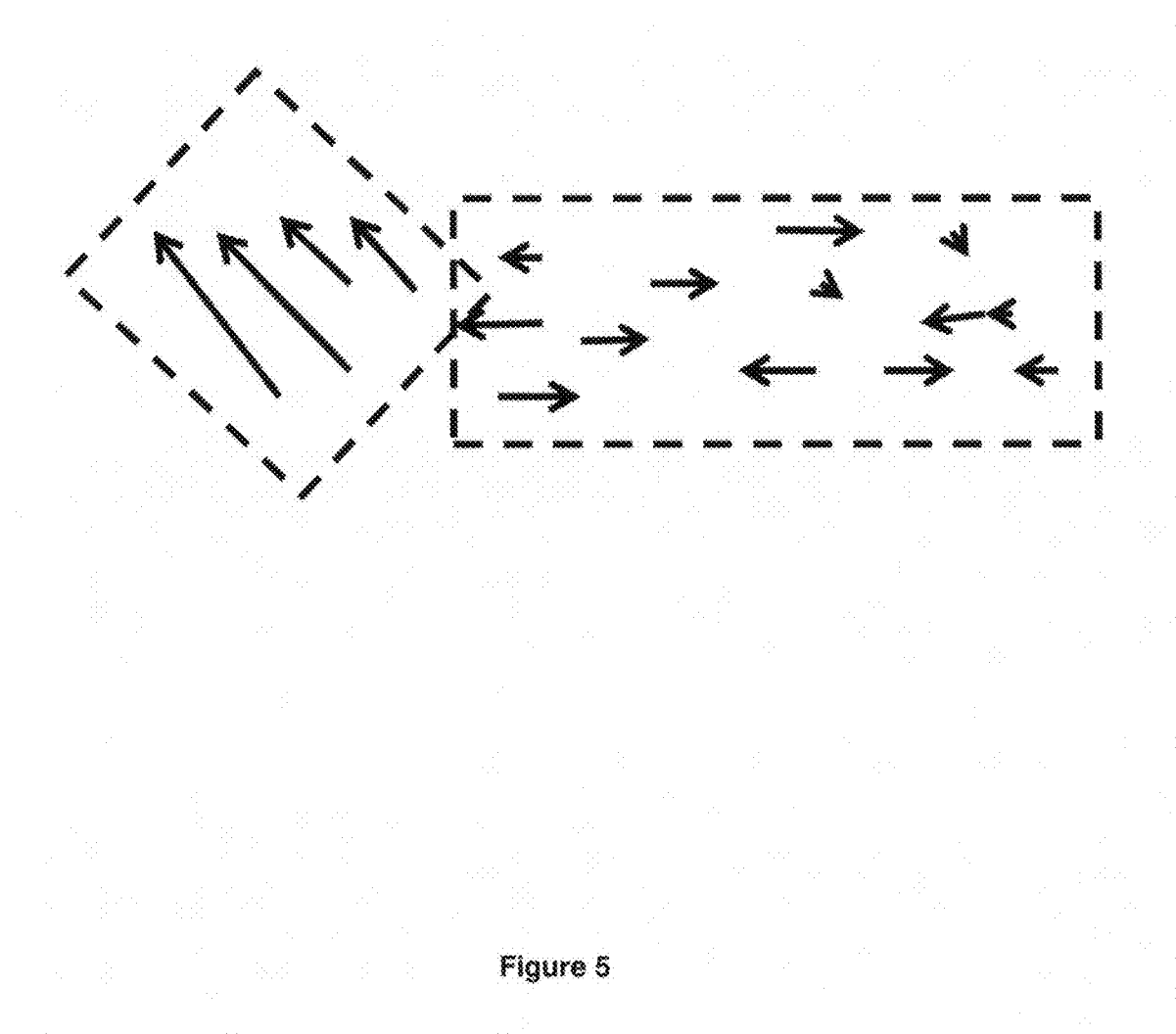
FIG. 5 is a schematic representation of two regions obtained from different scans, representing a patient's head on a rest in one scan, and lying flat in a previous scan.

In the present embodiment, the clustering technique specifically includes the curl of the vector field to determine regions of relative rotation. FIG. 5 provides a schematic representation of two regions obtained from different scans. One of the regions represents a patient's head on a rest in one scan, but lying flat in a previous scan.

In the embodiment of FIG. 3, the registration unit 36 at stage 44 determines, for each of the determined regions, a rigid registration that approximates the global non-rigid registration at that region. For each region, a value of rotation (for example, the value of a rotation parameter of the rigid or affine registration) is determined from the variational clustering (for example from a value of at least one rotational parameter), and a translation (for example the value of a translation parameter of the rigid or affine registration) is determined from the deformation field (for example from the value of a deformation field parameter) at the region in question. In variants of the embodiment a variation in scale is also determined, for example from an estimated divergence of the deformation field. The determined values of the rotation and translation (and scale, if used) are then combined to produce the rigid registration for the region.

Figure 6:
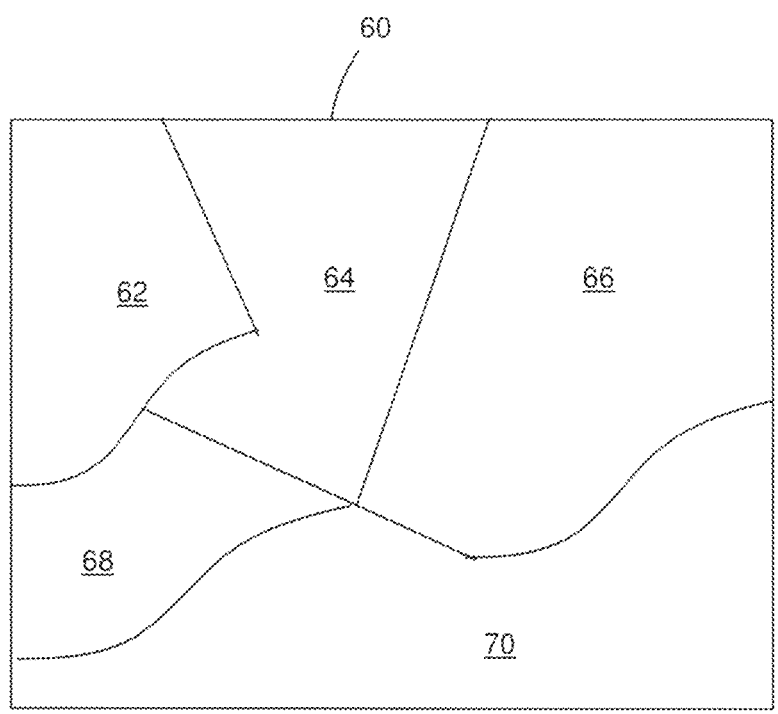
FIG. 6 is a schematic representation of an area that is registered to another scan by a global non-rigid registration, and that has been divided into regions.

FIG. 6 shows a schematic representation of the area 60 of a scan that is registered to another scan by a global non-rigid registration. The area has been divided into regions 62, 64, 66, 68, 70 using the variational clustering technique, and a rigid registration has been determined for each region 62, 64, 66, 68, 70, with the rigid registration for a particular region providing an approximation within a predetermined measure of accuracy of the non-rigid registration for points within that region. The scan area 60 is represented as two-dimensional in FIG. 6 for ease of representation, but it will be understood that the scan may be a three dimensional scan and the regions 62, 64, 66, 68, 70 may be three dimensional regions. In some embodiments, the regions are selected so that they substantially fill the volume represented by one or both of the image data sets. The regions may be contiguous or overlapping.

At the next stage 46, at least $1^{st}$ and $2^{nd}$ images are derived from the $1^{st}$ and $2^{nd}$ image data sets, either automatically or upon command of the user, and displayed together on the display device 24. In this case the images are MPR renderings of slices through the volumetric image data sets, and are displayed side-by-side.

Figure 7:
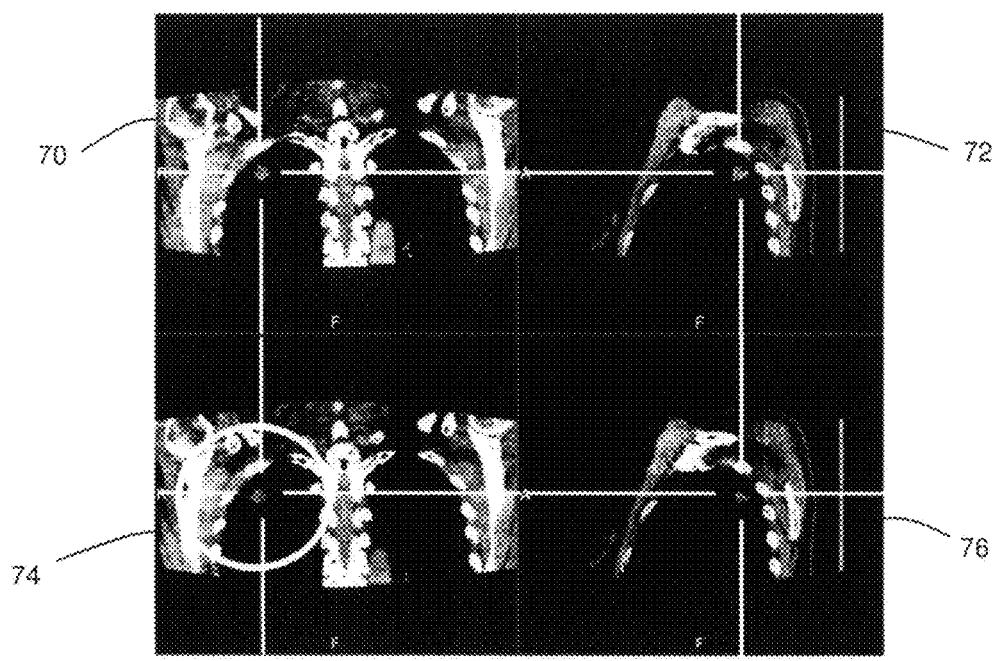
FIG. 7 shows images of two image slices obtained from each of a current scan and a prior scan.

In the example of FIG. 7, images of two orthogonal slices 70, 72 obtained from the $1^{st}$ image data set (current scan) and representing the same anatomical region of the lung are displayed side-by-side, and above corresponding orthogonal slices 74, 76 obtained from the $2^{nd}$ image data set (prior scan). The image 70 is centred around a point of interest that, in this case, is at the centre of the crosshairs shown on the image 70.

The orthogonal slices 74, 76 from the $2^{nd}$ image data set are selected for display as representing the same region of anatomy as the slices 70, 72. The slices 74, 76 are selected by determining the regions of the $2^{nd}$ image data set that correspond to the regions of the $1^{st}$ image data set represented by slices 70, 72, by selecting and using the rigid registration that pertains at the point of interest. For example the registration unit 36 may transform the co-ordinates of the point of interest based on the rigid registration in question and the image data processing unit 34 may then render image data from the $2^{nd}$ image data set around a position determined from the transformed co-ordinates to generate and display the slices 74, 76. Thus, the images from the 1$^{st}$ and 2$^{nd}$ image data sets may be aligned based on the local rigid registration.

The user may then, for example, wish to navigate through the images, for instance move a point of interest or image area through the volume represented by the image data sets. For example, the user may wish to move to a new position in a direction extending orthogonally into the plane of the slice 70. In that case, it can be understood that the co-ordinates of the point of interest will change. The image data processing unit 34 will then process the 1$^{st}$ image data set to render and display new slices 70, 72 of the current scan corresponding to the new position. The process of the preceding paragraph is repeated to determine the regions of the 2$^{nd}$ image data set that correspond to the regions of the 1$^{st}$ image data set represented by new slices 70, 72, by using the previously selected rigid registration. Thus, the navigation of the images can be synchronised, such that in this case substantially the same anatomy is displayed in substantially the same position in each image at substantially the same time. Thus, the images may continue to be aligned during navigation.

The processes of the preceding two paragraphs can be performed continuously as a user scrolls or otherwise navigates through images, thus providing a continuous or quasi-continuous synchronised updating of the images.

Similar procedures to those described in the preceding three paragraphs can also be used to provide synchronous movement of the crosshairs, or other display indicator such as a cursor or pointer. In that case, the non-rigid registration that pertains at the point of interest is used to transform the position of the crosshairs or other display indicator on the images 70, 72 to determine the corresponding position for the crosshairs of the display indicator on the images 74, 76. Thus, it can be ensured that the crosshairs or other display indicator are positioned at the same anatomical position in each of the images.

It can be understood from the previous two paragraphs that in the described mode of operation, synchronised navigation (either of the images or of the display indicator) is achieved using the local rigid registration rather than the global non-rigid registration. That use of the local rigid registration can ensure that the navigation is smooth and intuitive for the user, without skipping of images or unexpected jumps. As the local rigid registration has been determined by the processes at stage 44 to be an accurate approximation of the non-rigid registration for the region in question, it can ensured that the synchronised navigation is also accurate.

It will be understood that if navigation is across a sufficiently large distance (either movement of the display indicator or navigation through the images) the point of interest may move outside the region where the selected local rigid registration is an accurate approximation of the global non-rigid registration.

For example, with reference to FIG. 6, if the point of interest were to begin in region 64, the local rigid registration pertaining in that region would be used to provide synchronised navigation (either navigation through the images, or movement of a display indicator) as described. If the point of interest were then to move to region 62 (for example if the display indicator was moved to region 62, or images centred around the point of interest were displayed) the selected rigid registration may no longer be an accurate approximation of the non-rigid registration. Thus, at stage 50, the embodiment provides for update of the rigid registration. For example, in the example of the present paragraph, the rigid registration selection may be updated to use the rigid registration pertaining at region 62 rather than that pertaining at region 64.

The update of the rigid registration may be performed in response to a user instruction, or automatically, according to embodiments.

Figure 8A:
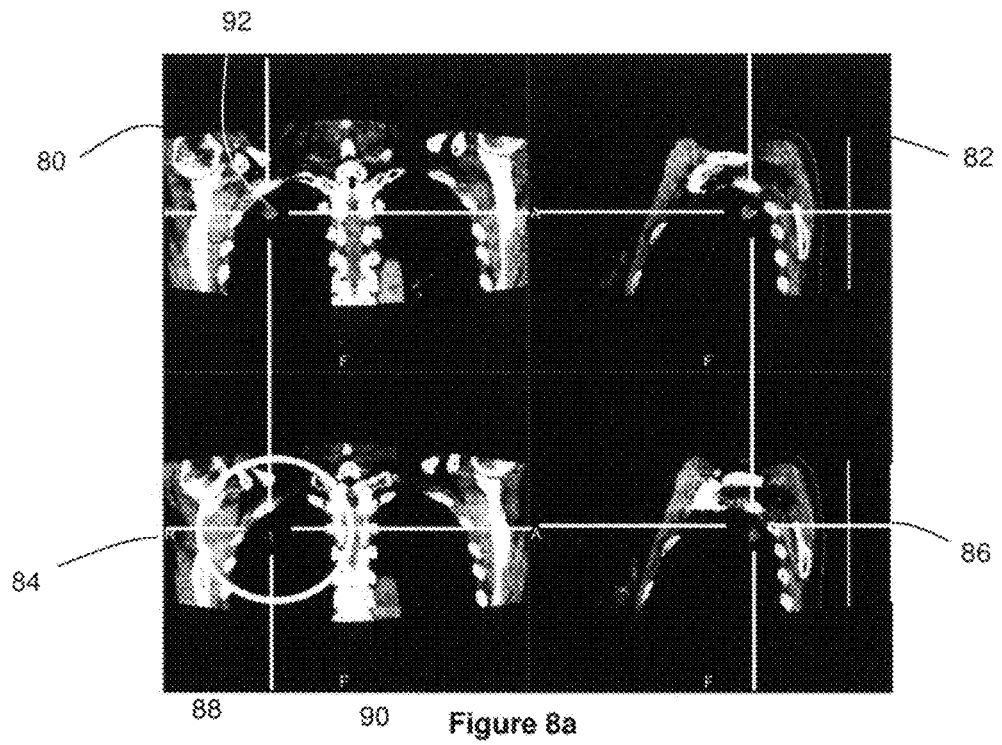
FIGS. 8a and 8b each shows images of two aligned sets of image slices obtained from a current scan and a prior scan, before and after manual updating of a local rigid registration.

FIG. 8*a* shows, images of two orthogonal slices 80, 82 obtained from the 1$^{st}$ image data set (current scan) and representing the same anatomical region displayed side-by-side, and above corresponding orthogonal slices 84, 86 obtained from the 2$^{nd}$ image data set (prior scan). The image 80 is centred around a point of interest.

Figure 8B:
Figure 8B:
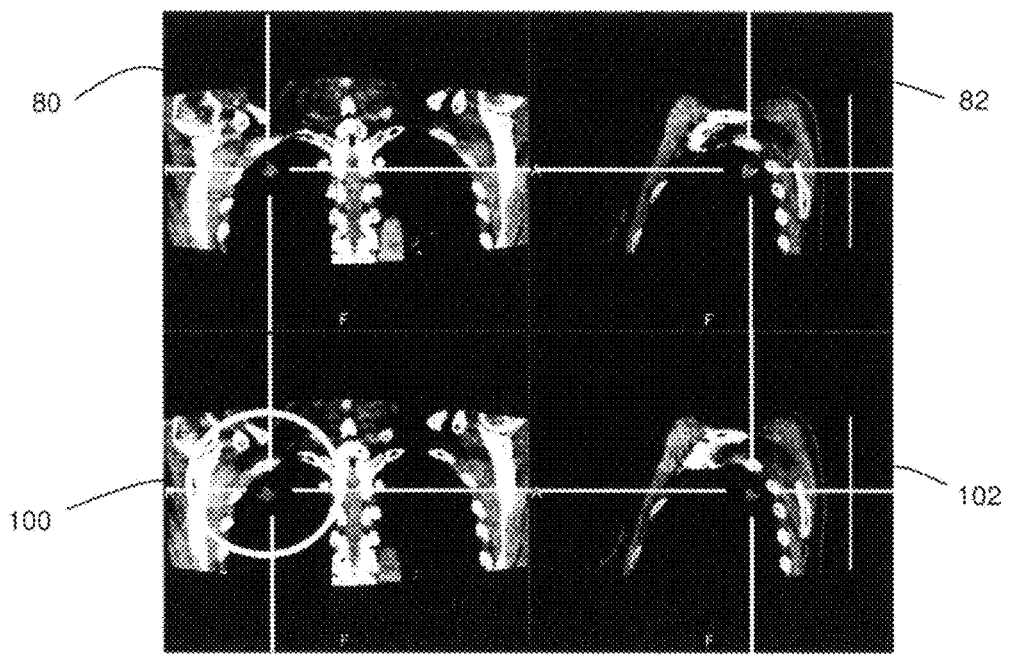

As with the example of FIG. 8, the slices 84, 86 have been selected based on use of the selected local rigid registration so that the slices 84, 86 should represent corresponding anatomical features to those of slices 80, 82. However, in this case slices 80, 82, 84, 86 are displayed following navigation by a user a significant distance from the initial position of the point of interest, in respect of which the original selection of the local rigid registration was made. The position of the point of interest is now outside the region where the original, selected local rigid registration accurately approximates the non-rigid registration.

In the embodiment described with reference to FIGS. 8*a* and 8*b*, the system is configured not to update the local rigid registration automatically and instead relies on user input to update the local rigid registration. In this case, the user notes that the anatomical feature 88 highlighted by the circle 90 in the image 84 is significantly different from the corresponding anatomical feature 92 in the image 80, and suspects that the registration has become inaccurate. The user then provides input, for example an appropriate key, mouse button press or selection from a menu, to update the registration.

In response to the user input, the registration unit 36 compares the current position of the point of interest (for example determined as being at the centre of image 80, or being represented by the cross hairs) to the locations of the various regions (for example regions 62, 64, 66, 68, 70 of FIG. 6) where the various local rigid registrations pertain. In this case, the point of interest has moved to a region where a new local rigid registration pertains. The registration unit 36 updates the selection of the local rigid registration so that the local rigid registration of the region corresponding to the new position of the point of interest is now used, and the images are then updated using the new local rigid registration. In this case that causes image slices 84, 86 to be replaced by image slices 100, 102 that are better registered to images slices 80, 82.

In an alternative mode of operation, the location of the point of interest is defined as being at the position of the cross hairs or other device indicator on image 80 rather than at the centre of the image 80. In that case, the user may move the cross hairs or other indicator over a point at which they wish the anatomical features from the different scans to be well aligned and then provide the user input instructing the registration unit 36 to update the images using the local rigid registration pertaining at that selected point of interest.

By providing updates of the local rigid registration in response to user input, rather than fully automatically in response to movement of a point of interest, it may be ensured that a user is not to be taken by surprise by unexplained or unexpected jumps in the images or position of a display indicator during navigation. The embodiment can also avoid the inconvenience to a user of adjusting the registration manually. Instead the selection of the local rigid registration can be updated automatically in response to the user input.

In the embodiment or mode of operation described with reference to FIGS. 8a and 8b, a specific request (command invoked) by the operator may update registration for the currently displayed anatomy. A crosshair, cursor or other display indicator may be used to indicate the point of interest, and the local rigid registration (and corresponding translation) may be updated so that anatomy is aligned. In alternative embodiments or modes of operation, the selection of the local rigid registration is updated automatically without user selection of such update.

Figure 9A:
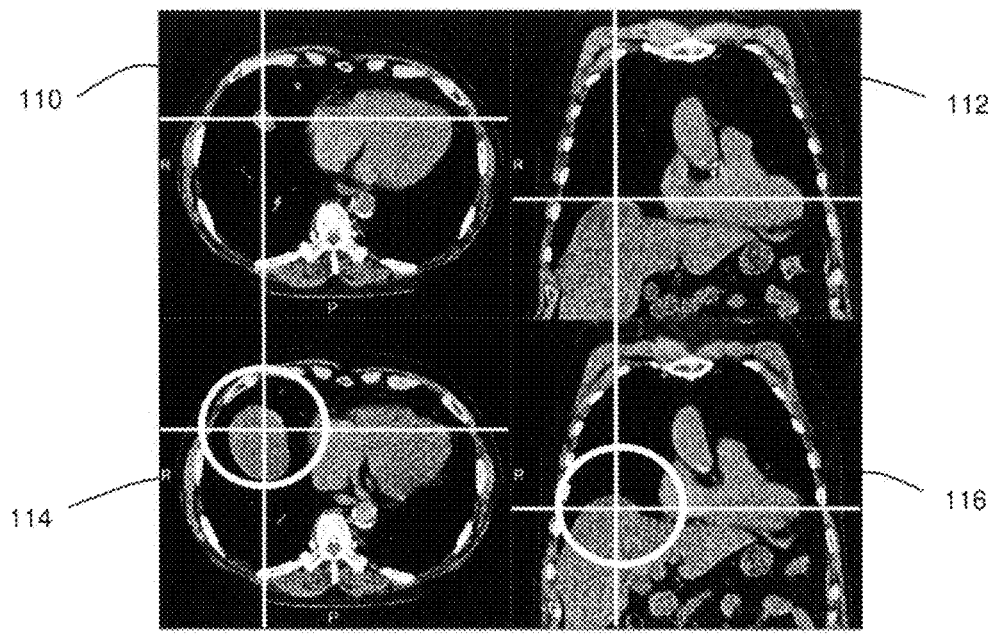
FIGS. 9a and 9b each shows images of two aligned sets of image slices obtained from a current scan and a prior scan, before and after automatic updating of a local rigid registration.
Figure 9B:
Figure 9B:
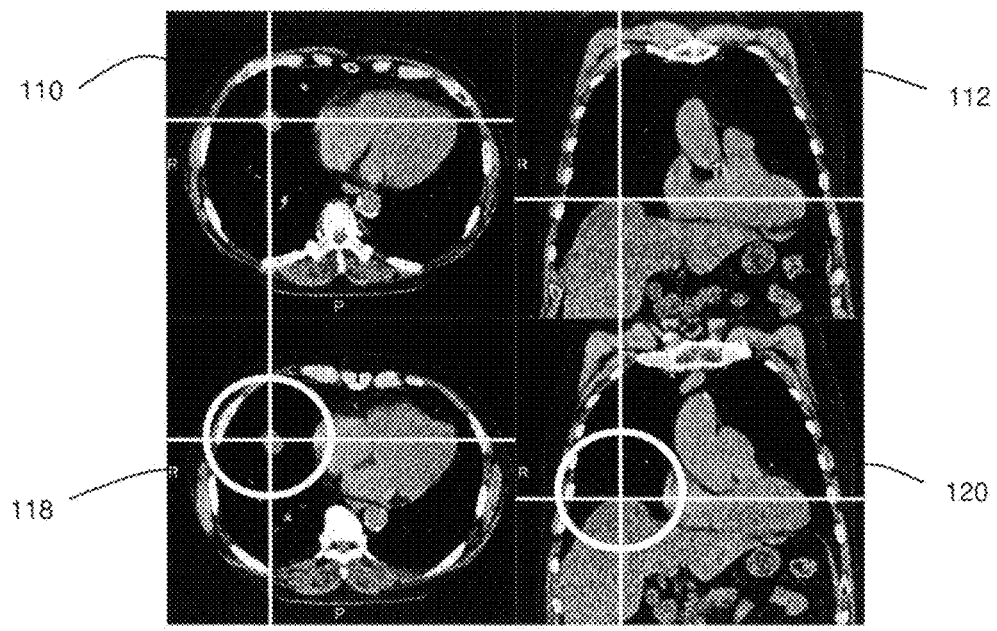

FIG. 9b shows images of two orthogonal slices 110, 112 obtained from the $1^{st}$ image data set (current scan) and representing the same anatomical region displayed side-by-side, and above corresponding orthogonal slices 114, 116 obtained from the $2^{nd}$ image data set (prior scan). The image 110 is centred around a point of interest.

In this case, the user has moved a significant distance by making a navigation jump from the images displayed in FIG. 7 to display a new region of anatomy as shown in FIG. 9b. The registration unit 36 has automatically detected that the position of the point of interest is now outside the region where the original, selected local rigid registration accurately approximated the non-rigid registration, and has automatically selected a new local rigid registration that corresponds to the new point of interest (in this case the centre of image 110). The point of interest has moved to a new local cluster automatically invoking a change in the local rigid registration.

FIG. 9a shows the images that would have been displayed if the registration unit 36 had not automatically updated the local rigid registration in response to movement outside the original region, and had continued to use the original selected rigid registration. Different image slices 114, 116 from the $2^{nd}$ image data set (prior scan) would have been displayed in place of images 118, 120, and would not correspond as well to images 110, 112 from the $1^{st}$ image data set. Furthermore, as can be seen in the right hand images (images 112, 116), the position of the cross-hairs would not correspond well to the position of the cross-hairs relative to anatomical features in the current and prior scans. In contrast, the positions of the cross-hairs relative to anatomical features correspond well between images 112 and 120 (current and prior scans) when the automatically updated local rigid registration is used.

In the embodiment of FIG. 3, the facility to automatically update the local rigid registration can be enabled or disabled. In one configuration, the automatic update is enabled for navigational leaps, when there is a navigation (of images or display indicator) of greater than a predetermined amount in a single step, but disabled for scrolling or movie operations. In the case of continuous scrolling or cine, the functionality described in relation to FIGS. 8a and 8b, enabling a user to request update of the selected local rigid registration may be enabled.

In embodiments the updating of the local rigid registration may be performed automatically in response to various conditions, for example in response to the navigation being navigation by greater than a predetermined distance; the movement of the display indicator being by greater than a predetermined distance; the navigation being from a first one of the regions, in which a first rigid or affine registration approximates the non-rigid registration, to a second one of the regions, in which a second rigid or affine registration approximates the non-rigid registration; the movement of the display indicator being from a first one of the regions, in which a first rigid or affine registration approximates the non-rigid registration, to a second one of the regions, in which a second rigid or affine registration approximates the non-rigid registration.

The dividing of the volume into regions may be subject to pre-determined constraints. For example, the dividing of the volume into regions may be subject to a constraint that the number of regions is fixed, and the procedure may then vary the size and boundary of the regions to obtain the best overall approximation of the non-rigid registration using the rigid or affine registrations associated with the regions.

Alternatively, the dividing of the volume into regions may be subject to a constraint that the number of regions is minimised whilst ensuring that for each region the rigid or affine registration approximates the non-rigid registration within a predetermined measure of accuracy.

The dividing of the volume into regions may also be subject to the constraint that the regions completely fill the volume represented by the image data sets.

Determination of approximately homogenous regions of the deformation field, as described in relation to the embodiment of FIG. 3, can avoid the user being required to specify a region of interest, and can ensure that rotation is seamlessly included. In alternative embodiments, any other suitable methods may be used to identify regions for which a non-rigid approximation may be approximated by a rigid or affine registration.

In embodiments, the non-rigid registration can be used to transform the position of a point of interest, as described, in order to select aligned images for display or to align the position of a display indicator between images. Those processes can be performed, as described, without transforming the image data itself, for example without transforming image data voxel by voxel. By using the original, non-transformed images the images may, in some cases, more reliably be used for diagnostic purposes.

Embodiments may provide a method of defining regions with approximately accurate affine transforms from non-rigid registration between two sets of volumetric medical image data (for example CT, MR or other types of medical image data) consisting of first computing the (for example, non-linear) deformation field (non-rigid registration), using a variational technique to determine approximately homogenous regions of the vector field (and the curl of the vector field). The regions and approximate affine transforms may be applied in synchronous study navigation (at least two volumes concurrently) when visualised with some form of reading software. The clustering of the curl of the deformation field may be used to determine the local rotation. The deformation field may be used to compute an appropriate translation. Study navigation may proceed with an initial estimate of the affine transform until the user makes a specific invocation to update the affine transform. Alternatively, study navigation may (optionally) automatically update the estimate of the affine transform when the user has navigated through a given number of approximately homogenous regions.

The embodiment of FIG. 3 has been described in relation to the processing of CT data. Any other suitable medical image data may be used in alternative embodiments, for example any type of CT data, for instance CT angiography data, MRI data, or PET data.

Embodiments have been described in relation to the approximation of the non-rigid registration by a rigid registration. In alternative embodiments the non-rigid registration may be approximated by other affine registrations, which may or may not be rigid registrations.

It will be well understood by persons of ordinary skill in the art that whilst some embodiments may implement certain functionality by means of a computer program having computer-readable instructions that are executable to perform the method of the embodiments, the computer program functionality could be implemented in hardware (for example by means of a CPU or by one or more ASICs (application specific integrated circuits)), FPGAs (field programmable gate arrays) or GPUs (graphic processing units) or by a mix of hardware and software.

Whilst particular units have been described herein, in alternative embodiments, functionality of one or more of those units can be provided by a single unit, processing resource or other component, or functionality provided by a single unit can be provided by two or more units or other components in combination. Reference to a single unit encompasses multiple components, for example units, providing the functionality of that unit, whether or not such components are remote from one another, and reference to multiple units encompasses a single component, for example unit, providing the functionality of those units.

While certain embodiments have been described, these embodiments have been presented by way of example only, and are not intended to limit the scope of the inventions. Indeed the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms and modifications as would fall within the scope of the invention.

The invention claimed is:

1. A medical image data processing apparatus comprising: circuitry configured to:
    perform a non-rigid registration of a first set of medical image data and a second set of medical image data, wherein each of the first and second sets of medical image data is representative of a scan area or volume, and the performing of the non-rigid registration comprises determining a non-rigid deformation field,
    perform a cluster analysis to automatically determine a plurality of regions of the scan area or volume, such that, for each region of the plurality of regions, the non-rigid deformation field within the region is approximately homogeneous, and
    determine, for each region of the plurality of regions, a respective rigid or affine registration that is an approximation of the non-rigid registration in the region.

2. The medical image data processing apparatus according to claim 1, wherein the circuitry is further configured to adjust boundaries of each region such that, for each region, the respective rigid or affine registration approximates the non-rigid registration within a predetermined measure of accuracy.

3. The medical image data processing apparatus according to claim 1, wherein the processing circuitry is configured to perform a variational clustering analysis as the cluster analysis.

4. The medical image data processing apparatus according to claim 3, wherein determining each rigid or affine registration comprises determining a rotation term of the rigid or affine registration from a rotation parameter of the variational clustering.

5. The medical image data processing apparatus according to claim 1, wherein determining each rigid or affine registration comprises determining a translation term of the rigid or affine registration from a deformation field parameter of the non-rigid registration.

6. The medical image data processing apparatus according to claim 1, wherein the determining of each rigid or affine registration comprises determining a rigid or affine registration that is an approximation of the non-rigid registration within a predetermined measure of accuracy.

7. The medical image data processing apparatus according to claim 6, wherein the determining of a region for which the initial registration is approximated by a rigid or affine registration within a predetermined measure of accuracy comprises comparing a measure of difference between an initial registration and the rigid or affine registration to a threshold.

8. The medical image data processing apparatus according to claim 1, wherein the plurality of regions fill a volume represented by at least one of the first set of medical image data set and the second set of medical image data.

9. The medical image data processing apparatus according to claim 1, further comprising a display,
    wherein the circuitry is further configured to at least one of:
        display using the display a first image obtained from the first medical image data set, and a second image obtained from the second image data set that, in accordance with the rigid or affine registration, corresponds to the first image; and
        display on a third image a first display indicator, display on a fourth image a second display indicator, wherein the position of the second display indicator on the fourth image corresponds to the position of the first display indicator on the third image according to the rigid or affine registration.

10. The medical image data processing apparatus according to claim 9, wherein the circuitry is further configured to at least one of:
    synchronize navigation of the second image to navigation of the first image in accordance with the rigid or affine registrations; and
    synchronize movement of the second display indicator to movement of the first display indicator in accordance with the rigid or affine registrations.

11. The medical image data processing apparatus according to claim 10, wherein the circuitry is further configured to update the rigid or affine registrations automatically in response to at least one of the following conditions:
    the navigation being navigation by greater than a predetermined distance;
    the movement of the display indicator being by greater than a predetermined distance;
    the navigation being from a first one of the regions, in which a first rigid or affine registration approximates the non-rigid registration, to a second one of the regions, in which a second rigid or affine registration approximates the non-rigid registration; and
    the movement of the display indicator being from the first one of the regions, in which the first rigid or affine registration approximates the non-rigid registration, to the second one of the regions, in which the second rigid or affine registration approximates the non-rigid registration.

12. The medical image data processing apparatus according to claim 11, wherein the automatic updating of the rigid or affine registration is disabled during scroll or movie operations.

13. The medical image data processing apparatus according to claim 10, wherein the navigation comprises movement of a point of interest.

14. The medical image data processing apparatus according to claim 13, wherein the point of interest is defined relative at least one of:
the center of the first image or the second image; and
the position of the first display indicator or the position of the second display indicator.

15. The medical image data processing apparatus according to claim 1, further comprising a user input device, wherein the circuitry is further configured to update the rigid or affine registrations in response to user input via the user input device.

16. The medical image data processing apparatus according to claim 15, wherein subsequent to the user input the updating of the rigid or affine registrations is performed automatically in response to at least one of the following conditions being satisfied:
navigation by greater than a predetermined distance;
movement of a display indicator being by greater than a predetermined distance;
the navigation being from a first one of the regions, in which a first rigid or affine registration approximates the non-rigid registration, to a second one of the regions, in which a second rigid or affine registration approximates the non-rigid registration; and
the movement of the display indicator being from the first one of the regions, in which the first rigid or affine registration approximates the non-rigid registration, to the second one of the regions, in which the second rigid or affine registration approximates the non-rigid registration.

17. The medical image data processing apparatus according to claim 1, further comprising a display, and wherein the circuitry is further configured to:
display on the display a first image derived from the first image data set and a second image derived from the second image data set;
select one of the rigid or affine registrations based on a position of a point of interest in one of the plurality of regions for which the deformation field is approximately homogeneous;
synchronize navigation of the first and second images or of a display indicator using the selected rigid or affine registration;
select a further one of the rigid or affine registrations following a movement of the point of interest into a further one of the plurality of regions for which the deformation field is approximately homogenous; and
synchronize the navigation of the first and second images or of the display indicator using the further selected rigid or affine registration in place of the selected rigid or affine registration.

18. A method of processing medical image data comprising:
performing a non-rigid registration of a first set of medical image data and a second set of medical image data, wherein each of the first and second sets of medical image data is representative of a scan area or volume, and the performing of the non-rigid registration comprises determining a non-rigid deformation field;
performing a cluster analysis to automatically determine a plurality of regions of the scan area or volume, such that, for each region of the plurality of regions, the non-rigid deformation field within the region is approximately homogeneous; and
for each region of the plurality of regions, determining a respective rigid or affine registration that is an approximation of the non-rigid registration in the region.

19. A computer program product comprising machine-readable instructions that are executable to perform the method according to claim 18.

* * * * *